US012399363B2

(12) United States Patent
Taylor et al.

(10) Patent No.: US 12,399,363 B2
(45) Date of Patent: Aug. 26, 2025

(54) INEBRIATION TEST SYSTEM

(71) Applicant: Ford Global Technologies, LLC, Dearborn, MI (US)

(72) Inventors: Alexandra Taylor, Harbor Springs, MI (US); Ali Hassani, Ann Arbor, MI (US); Mohammad Hassani, Ann Arbor, MI (US); Justin Miller, Berkley, MI (US); John Robert Van Wiemeersch, Novi, MI (US)

( * ) Notice: Subject to any disclaimer, the term of this patent is extended or adjusted under 35 U.S.C. 154(b) by 457 days.

(21) Appl. No.: 18/049,916

(22) Filed: Oct. 26, 2022

(65) Prior Publication Data

US 2024/0142777 A1 May 2, 2024

(51) Int. Cl.
*B60K 28/06* (2006.01)
*A61B 3/113* (2006.01)
(Continued)

(52) U.S. Cl.
CPC ............ *G02B 27/017* (2013.01); *A61B 3/113* (2013.01); *A61B 5/163* (2017.08); *A61B 5/18* (2013.01);
(Continued)

(58) Field of Classification Search
CPC .............. G02B 2027/014; G02B 27/01; G02B 27/0093; B60K 28/063; B60K 28/066;
(Continued)

(56) References Cited

U.S. PATENT DOCUMENTS 8,226,574 B2 * 7/2012 Whillock ............. A61B 5/4863
351/210
9,475,387 B2 10/2016 Wu
(Continued)

FOREIGN PATENT DOCUMENTS

CN 102785574 B 4/2015
CN 102975721 B 9/2016

OTHER PUBLICATIONS

Guoliang Yuan et al., A Novel Driving Behavior Learning and Visualization Method with Natural Gaze Prediction, IEEE Access, vol. 9, Jan. 27, 2021, 18560-18568.
(Continued)

*Primary Examiner* — Keith J Frisby
(74) *Attorney, Agent, or Firm* — Frank Lollo; Eversheds Sutherland (US) LLP

(57) ABSTRACT

A method to prevent intoxicated operation is described. The method includes providing instructions to a vehicle user to position a vehicle user body portion posture in a predefined alignment. The method further includes obtaining the vehicle user body portion posture from a first vehicle detector, and determining whether the vehicle user body portion posture is in the predefined alignment. The method includes activating a plurality of vehicle visual indicators to illuminate in a predefined manner when the vehicle user body portion posture is in the predefined alignment. The method further includes providing instructions to the vehicle user to move vehicle user eyes to track the plurality of vehicle visual indicators, and obtaining a vehicle user eye movement from a second vehicle detector. The method further includes determining whether the vehicle user eye movement meets a predetermined condition, and actuating a control action accordingly.

20 Claims, 6 Drawing Sheets

(51) Int. Cl.
*A61B 5/00* (2006.01)
*A61B 5/16* (2006.01)
*A61B 5/18* (2006.01)
*B60W 40/08* (2012.01)
*B60W 50/14* (2020.01)
*G02B 27/00* (2006.01)
*G02B 27/01* (2006.01)
*G06V 10/141* (2022.01)
*G06V 20/59* (2022.01)

(52) U.S. Cl.
CPC ............ *A61B 5/6893* (2013.01); *B60K 28/06* (2013.01); *B60K 28/063* (2013.01); *B60K 28/066* (2013.01); *B60W 50/14* (2013.01); *G02B 27/0093* (2013.01); *G06V 10/141* (2022.01); *G06V 20/597* (2022.01); *B60W 2040/0836* (2013.01); *B60W 2540/223* (2020.02); *B60W 2540/24* (2013.01); *B60W 2556/45* (2020.02); *B60W 2756/10* (2020.02); *B60Y 2302/01* (2013.01); *G02B 2027/014* (2013.01)

(58) Field of Classification Search
CPC .......... B60K 28/06; B60W 2040/0818; B60W 2040/0836; B60W 2040/0845; B60W 40/08; B60W 2540/24; B60W 2540/26; B60W 2540/223; B60W 50/14; B60W 2556/45; B60W 2756/10; A61B 5/163; A61B 5/18; A61B 5/4845; A61B 5/4863; A61B 5/6893; A61B 3/113; G06V 20/597; G06V 10/141; B60Y 2302/01
USPC .................. 180/271, 272; 340/576; 351/209
See application file for complete search history.

(56) References Cited

U.S. PATENT DOCUMENTS

| | | | |
|---|---|---|---|
| 10,089,543 B2 * | 10/2018 | Fung | G06V 40/168 |
| 10,343,693 B1 | 7/2019 | Plummer et al. | |
| 10,390,802 B1 * | 8/2019 | Picard | A61B 3/113 |
| 2007/0132950 A1 * | 6/2007 | Victor | A61B 3/1015 |
| | | | 351/200 |
| 2010/0280372 A1 * | 11/2010 | Poolman | A61B 5/4094 |
| | | | 600/407 |
| 2010/0294583 A1 * | 11/2010 | Biondo | A61B 5/082 |
| | | | 340/576 |
| 2015/0158495 A1 * | 6/2015 | Duncan | G08G 1/163 |
| | | | 701/1 |
| 2015/0258892 A1 * | 9/2015 | Wu | G06V 40/166 |
| | | | 340/576 |
| 2016/0339922 A1 * | 11/2016 | Schmidt | B60W 40/08 |
| 2017/0049362 A1 * | 2/2017 | Macknik | A61B 5/163 |
| 2017/0105669 A1 * | 4/2017 | Valenti | A61B 3/0025 |
| 2018/0301225 A1 | 10/2018 | Nothacker et al. | |
| 2018/0339706 A1 * | 11/2018 | Biondo | B60W 50/10 |
| 2021/0200991 A1 * | 7/2021 | Prins | G06V 40/19 |
| 2021/0291650 A1 * | 9/2021 | Minjeur | A61B 5/0002 |
| 2021/0316737 A1 * | 10/2021 | Iwase | A61B 5/4035 |
| 2021/0394764 A1 * | 12/2021 | Clines | G06F 16/93 |
| 2022/0153302 A1 * | 5/2022 | Arechiga-Gonzalez | |
| | | | B60W 50/14 |
| 2023/0233120 A1 * | 7/2023 | Fichtler | A61B 5/7264 |
| | | | 600/301 |
| 2024/0185636 A1 * | 6/2024 | Prins | G06V 10/141 |

OTHER PUBLICATIONS

Mnay K Diddi1 et al., Head Pose and Eye State Monitoring (HEM) for Driver Drowsiness Detection: Overview, JISET—International Journal of Innovative Science, Engineering & Technology, vol. 1, Issue 9, Nov. 9, 2014, 504-508.

* cited by examiner

INEBRIATION TEST SYSTEM

TECHNICAL FIELD

The present disclosure relates to mitigating incidents of intoxicated driving, and more particularly, for vehicle systems that test for driver inebriation using eye gaze.

BACKGROUND

Government and private entities frequently implement initiatives that prevent intoxicated operation of motor vehicles. For example, state and federal agencies may provide driver awareness programs. Some corporations educate employees on driver inebriation consequences, and schools and colleges frequently teach their students negative outcomes associated with intoxicated vehicle operation. Even with these initiatives, some vehicle drivers may still choose to operate vehicles while intoxicated despite efforts to minimize such instances.

Authorities implement various approaches to detect driver inebriation. One conventional approach includes the use of a breath analyzer. The breath analyzer measures an alcohol amount in a person's breath and helps to minimize intoxicated operation of vehicles. Typically, enforcement officers, e.g., police officers, use breath analyzers to test vehicle drivers' breath, and prevent the drivers from driving their vehicles if the breath indicates alcohol presence. This approach of preventing intoxicated operation is effective; however, implementation of education and enforcement measures are limited. In addition, a separate apparatus, for example, the breath analyzer, is required to test the drivers' breath. Therefore, this approach may not always be practical, and may be limited in its utility due to logistical and/or bandwidth constraints.

Another conventional approach is the use of a field sobriety test that includes a horizontal gaze nystagmus test. To take the horizontal gaze nystagmus test, a police officer may ask the vehicle driver to track movement of an object, such as a flashlight or a pen, from side to side. As the vehicle driver tracks the object movement and rotates his eyes, eye twitching may occur at extreme eye poses, and/or eye movement may become irregular. The police officer may detect driver inebriation when eye twitching and/or irregular eye movement occurs. Although this approach does not require a separate apparatus (e.g., the breath analyzer), this approach too is limited by police officers' bandwidth/availability.

Thus, there still exists a need in the industry for a system and method for preventing intoxicated operation, specifically for determining driver inebriation and executing control actions.

It is with respect to these and other considerations that the disclosure made herein is presented.

BRIEF DESCRIPTION OF THE DRAWINGS

The detailed description is set forth with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

Figure 1:
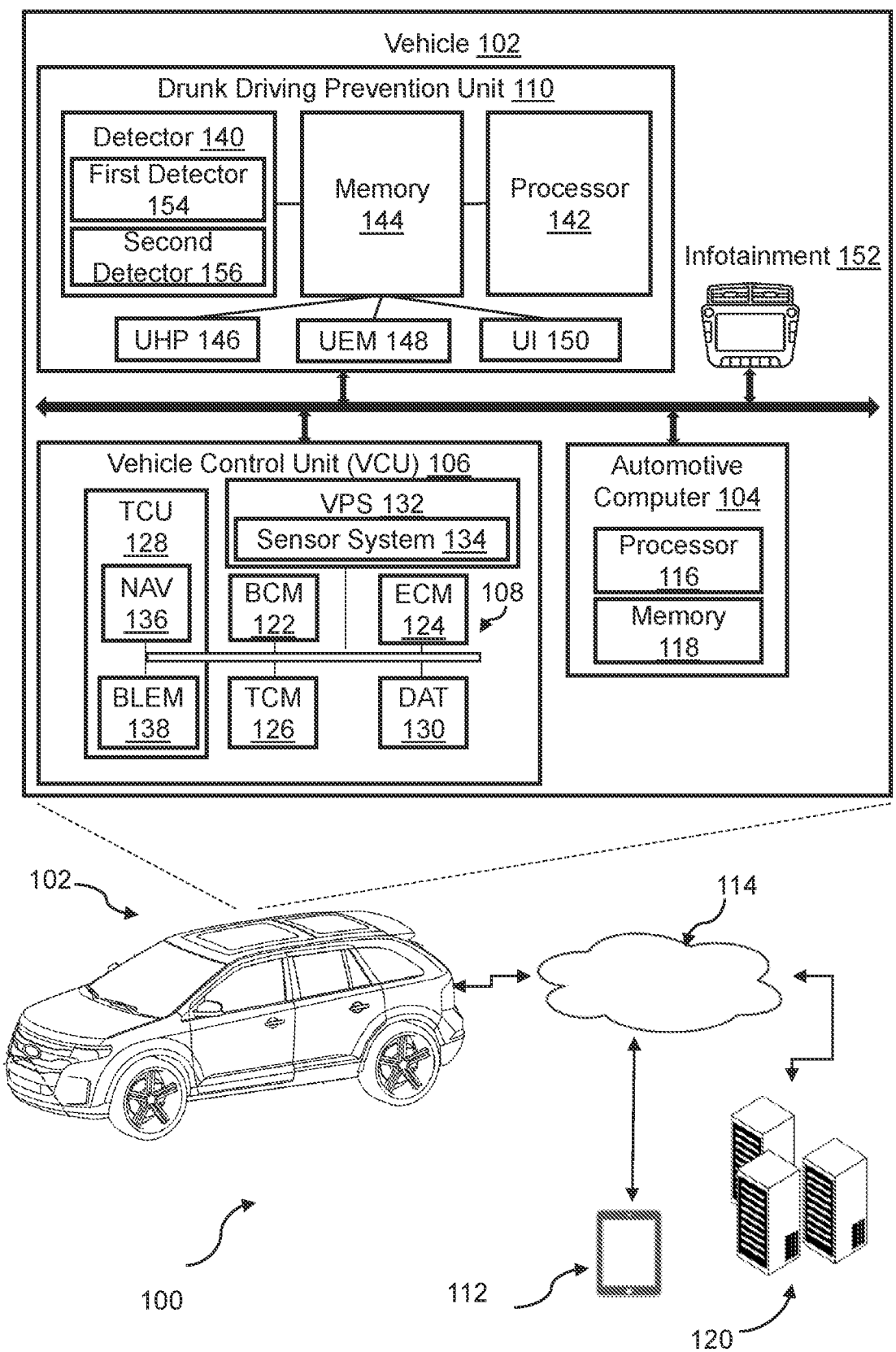
FIG. 1 depicts an example system to prevent intoxicated operation of a vehicle, in accordance with the present disclosure.

The present disclosure describes a system and method to reduce or prevent instances of vehicle operation while intoxicated, whether through consumption of alcohol or some other substance that would impairs one's ability to safely operate a vehicle. In particular, the present disclosure describes a system configured and/or programmed to coach a vehicle user to perform an inebriation test (such as a horizontal eye gaze nystagmus test) inside a vehicle. In some aspects, a vehicle processor may provide an instruction (also referred to as output or feedback) to the vehicle user to position user's head in a predetermined alignment, for example, a straight head position aligned towards a vehicle steering wheel.

Responsive to the vehicle user positioning her/his head in the predetermined alignment, the vehicle processor may activate a plurality of vehicle visual Human-Machine Interface (HMI) components in a predefined manner. For example, the vehicle processor may activate the visual HMI components in a sequential manner, from one vehicle end (e.g., a left vehicle end) to another (e.g., a right vehicle end).

In some aspects, the vehicle processor may provide another instruction to the vehicle user to track the plurality of vehicle visual HMI components by using vehicle user eyes, without moving the head. The vehicle processor may determine whether a vehicle user eye movement (during the tracking) meets a predetermined condition and may actuate one or more control action(s). In some aspects, the vehicle processor may determine that the vehicle user is in an inebriated state when the vehicle user eye movement meets the predetermined condition.

The predetermined condition can include eye twitching at extreme eye gazes or an irregular eye tracking when the vehicle user eyes track the plurality of vehicle visual HMI components.

In some aspects, responsive to a determination that the vehicle user is in the inebriated state, the vehicle processor may actuate the control action(s). The control action(s) may include disabling a vehicle start, transmitting a vehicle user inebriated state notification to an acquaintance user device or a vehicle ridesharing server, providing an instruction to a non-inebriated vehicle passenger to drive the vehicle, and/or calling authorities (for example, the police).

In some aspects, the vehicle processor may trigger the inebriation test when the vehicle user enters the vehicle or based on trigger events. The trigger events may include, for example, indication of distracted driving or other vehicle user behaviors. For instance, if the vehicle user is swerving, feeling drowsy or fatigued, the vehicle processor may trigger the inebriation test. In some aspects, the vehicle user may trigger the inebriation test to confirm if the vehicle user is fit for driving. In further aspects, the inebriation test may be triggered automatically based upon user settings.

The present disclosure provides various advantages over the conventional approaches to mitigate or prevent intoxicated operation of a motor vehicle configured with the disclosed system. The vehicle may provide coaching to the vehicle user to take the inebriation test without involvement of any third party (such as enforcement officers or police officers). Further, the system does not require addition of a breath analyzer to detect a vehicle user inebriation state.

These and other advantages of the present disclosure are provided in detail herein.

Illustrative Embodiments

The disclosure will be described more fully hereinafter with reference to the accompanying drawings, in which example embodiments of the disclosure are shown, and not intended to be limiting.

FIG. 1 depicts a system 100 to prevent intoxicated operation, in accordance with the present disclosure. More particularly, FIG. 1 depicts the system 100 that may include a vehicle 102. The vehicle 102 may take the form of any passenger or commercial vehicle such as, for example, a car, a work vehicle, a crossover vehicle, a van, a minivan, a taxi, a bus, etc. In addition, the vehicle 102 may include other land vehicles (such as motorcycles, scooters etc.), marine vehicles (such as water scooter, jet skis, boats etc.,) and/or the like. Further, the vehicle 102 may be a manually driven vehicle, and/or may be configured to operate in a partially autonomous mode, and may include any powertrain such as, for example, a gasoline engine, one or more electrically actuated motor(s), a hybrid system, etc.

In some aspects, the vehicle 102 may include an automotive computer 104, a Vehicle Control Unit (VCU) 106, and an intoxicated operation prevention unit 110. The VCU 106 may include a plurality of Electronic Control Units (ECUs) 108 disposed in communication with the automotive computer 104.

The system 100 may further include a mobile device 112 that may connect with the automotive computer 104 and/or the intoxicated operation prevention unit 110 by using wired and/or wireless communication protocols and transceivers. In some aspects, the mobile device 112 may be associated with a vehicle user/operator (not shown in FIG. 1). In other aspects, the mobile device 112 may be associated with other users (not shown in FIG. 1). The mobile device 112 may communicatively couple with the vehicle 102 via one or more network(s) 114, which may communicate via one or more wireless connection(s), and/or may connect with the vehicle 102 directly by using near field communication (NFC) protocols, Bluetooth® protocols, Wi-Fi, Ultra-Wide Band (UWB), and other possible data connection and sharing techniques.

The network(s) 114 illustrates an example communication infrastructure in which the connected devices discussed in various embodiments of this disclosure may communicate. The network(s) 114 may be and/or include the Internet, a private network, public network or other configuration that operates using any one or more known communication protocols such as, for example, transmission control protocol/Internet protocol (TCP/IP), Bluetooth®, Bluetooth® Low Energy (BLE), Wi-Fi based on the Institute of Electrical and Electronics Engineers (IEEE) standard 802.11, UWB, and cellular technologies such as Time Division Multiple Access (TDMA), Code Division Multiple Access (CDMA), High-Speed Packet Access (HSPDA), Long-Term Evolution (LTE), Global System for Mobile Communications (GSM), and Fifth Generation (5G), to name a few examples.

In some aspects, the automotive computer 104 and/or the intoxicated operation prevention unit 110 may be installed in a vehicle engine compartment (or elsewhere in the vehicle 102) and operate as an intoxicated operation prevention unit functional part, in accordance with the disclosure. The automotive computer 104 may be or include an electronic vehicle controller, having one or more processor(s) 116 and a memory 118. Moreover, the intoxicated operation prevention unit 110 may be separate from the automotive computer 104 (as shown in FIG. 1) or may be integrated as an automotive computer part.

The processor(s) 116 may be disposed in communication with one or more memory devices disposed in communication with the respective computing systems (e.g., the memory 118 and/or one or more external databases not shown in FIG. 1). The processor(s) 116 may utilize the memory 118 to store programs in code and/or to store data for performing aspects in accordance with the disclosure. The memory 118 may be a non-transitory computer-readable memory storing a vehicle intoxicated operation prevention program code. The memory 118 can include any one or a combination of volatile memory elements (e.g., dynamic random-access memory (DRAM), synchronous dynamic random-access memory (SDRAM), etc.) and can include any one or more nonvolatile memory elements (e.g., erasable programmable read-only memory (EPROM), flash memory, electronically erasable programmable read-only memory (EEPROM), programmable read-only memory (PROM), etc).

In some aspects, the automotive computer 104 may be disposed in communication with one or more server(s) 120, and the mobile device 112. The server(s) 120 may be part of a cloud-based computing infrastructure and may be associated with and/or include a Telematics Service Delivery Network (SDN) that provides digital data services to the vehicle 102 and other vehicles (not shown in FIG. 1) that may be part of a vehicle fleet.

In accordance with some aspects, the VCU 106 may share a power bus with the automotive computer 104 and may be configured and/or programmed to coordinate the data between vehicle 102 systems, connected servers (e.g., the server(s) 120), and other vehicles (not shown in FIG. 1) operating as part of a vehicle fleet. The VCU 106 can include or communicate with any combination of the ECUs 108, such as, for example, a Body Control Module (BCM) 122, an Engine Control Module (ECM) 124, a Transmission Control Module (TCM) 126, a telematics control unit (TCU) 128, a Driver Assistances Technologies (DAT) controller 130, etc. The VCU 106 may further include and/or communicate with a Vehicle Perception System (VPS) 132, having connectivity with and/or control of one or more vehicle sensory system(s) 134. In some aspects, the VCU 106 may control the vehicle 102 operational aspects and implement one or more instruction sets received from the application operating on the mobile device 112, from one or more instruction sets stored in the memory 118, including instruction sets stored in the intoxicated operation prevention unit 110.

The TCU 128 can be configured and/or programmed to provide vehicle connectivity to wireless computing systems onboard and off board the vehicle 102, and may include a Navigation (NAV) receiver 136 for receiving and processing a GPS signal, a BLE Module (BLEM) 138, a Wi-Fi transceiver, a UWB transceiver, a NFC transceiver and/or other wireless transceivers (not shown in FIG. 1) that may be configurable for wireless communication between the vehicle 102 and other systems, computers, and modules. The TCU 128 may be disposed in communication with the ECUs 108 by way of a bus.

In some aspects, the ECUs 108 may control aspects of vehicle operation and communication using inputs from human drivers, inputs from an autonomous vehicle controller, the intoxicated operation prevention unit 110, and/or via wireless signal inputs received via the wireless connection(s) from other connected devices, such as the mobile device 112, the server(s) 120, among others.

The BCM 122 generally includes integration of sensors, vehicle performance indicators, and variable reactors associated with vehicle systems, and may include processor-based power distribution circuitry that can control functions associated with the vehicle body such as lights, windows, security, camera(s), audio system(s), speakers, display system, door locks and access control, vehicle energy management, and various comfort controls. The BCM 122 may also operate as a gateway for bus and network interfaces to interact with remote ECUs (not shown in FIG. 1).

In some aspects, the DAT controller 130 may provide Level-1 through Level-3 automated driving and driver assistance functionality that can include, for example, active parking assistance, trailer backup assistance, adaptive cruise control, lane keeping, and/or driver status monitoring, among other features. The DAT controller 130 may also provide aspects of user and environmental inputs usable for user authentication.

The DAT controller 130 can further obtain input information via the vehicle sensory system(s) 134, which may include sensors disposed on the vehicle interior and/or exterior (sensors not shown in FIG. 1). The DAT controller 130 may receive the sensor information associated with driver functions, vehicle functions, and environmental inputs, and other information.

In some aspects, the automotive computer 104 may connect with an infotainment system 152 that may include a touchscreen interface portion, and may include voice recognition features, biometric identification capabilities that can identify users based on facial recognition, voice recognition, fingerprint identification, or other biological identification means. In other aspects, the infotainment system 152 may provide user identification using mobile device pairing techniques (e.g., connecting with the mobile device 212, a Personal Identification Number (PIN) code, a password, passphrase, or other identifying means).

The computing system architecture of the automotive computer 104, the VCU 106, and/or the intoxicated operation prevention unit 110 may omit certain computing modules. It should be readily understood that the computing environment depicted in FIG. 1 is an example of a possible implementation according to the present disclosure, and thus, it should not be considered limiting or exclusive.

In accordance with some aspects, the intoxicated operation prevention unit 110 may be executed as part of and/or integrated with the ECUs 108. The intoxicated operation prevention unit 110, regardless of whether it is integrated with the automotive computer 104 or the ECUs 108, or whether it operates as an independent computing system in the vehicle 102, may include a detection unit 140 (or detector(s) 140), a processor 142, and a computer-readable memory 144, which are communicatively coupled to each other. The detector(s) 140 may include a first detector 154 and a second detector 156.

In accordance with some aspects, the intoxicated operation prevention unit 110 may be configured to take an inebriation test of a vehicle user, for example a vehicle 102 driver (not shown in FIG. 1). In particular, the intoxicated operation prevention unit 110 may be configured to provide training to the vehicle user to take the inebriation test inside the vehicle 102 and actuate control actions accordingly. The details of the above-mentioned features may be understood as follows.

In some aspects, the intoxicated operation prevention unit 110 may actuate, via the processor 142, the vehicle user inebriation test when the vehicle user enters the vehicle 102 and/or when the processor 142 receives a trigger event, as discussed below.

In some aspects, the intoxicated operation prevention unit 110 may actuate the inebriation test whenever the vehicle user enters the vehicle 102 if the vehicle user has a history of intoxicated operation. In particular, the memory 118 and/or the memory 144 may store a vehicle user intoxicated operation history, and the processor 142 may fetch the history when the vehicle user enters the vehicle 102. In addition, or alternatively, the processor 142 may obtain the vehicle user intoxicated operation history from the server 120 (which may, for example, store intoxicated operation histories of a plurality of vehicle users). Responsive to obtaining the intoxicated operation history, the processor 142 may actuate the vehicle user inebriation test if the history shows repeated intoxicated operation instances.

In some aspects, the intoxicated operation prevention unit 110 may determine the vehicle user entry in the vehicle 102 via the sensory system 134. For example, the sensory system 134 may include vehicle occupancy sensors that may send a signal to the processor 142, when the vehicle user enters the vehicle 102. Responsive to receiving the vehicle user entry signal, the processor 142 may actuate the vehicle user inebriation test, as described above.

In another aspect, the intoxicated operation prevention unit 110 may actuate a general vehicle user focus test when the vehicle user enters the vehicle 102, before actuating the inebriation test. For example, the processor 142 may actuate the general vehicle user focus test, when the vehicle user does not have an intoxicated operation history. In this case, the processor 142 may instruct the vehicle user to take the general vehicle user focus test, and based on the focus test results, the processor 142 may actuate (or not actuate) the inebriation test. In one aspect, the processor 142 may actuate the inebriation test, when the vehicle user does not pass the general vehicle user focus test. The general vehicle user focus test details are described in conjunction with FIG. 3.

In another aspect, the processor 142 may actuate the vehicle user inebriation test when the processor 142 determines that the vehicle user is swerving while driving the vehicle 102. In particular, the processor 142 may determine whether the vehicle user is swerving the vehicle 102 via the DAT controller 130. For example, the DAT controller 130 may determine that the vehicle user is changing lanes frequently (e.g., above a predefined threshold in a preset period) and may send a signal associated with the frequency of lane changing to the processor 142. Responsive to receiving the lane-changing signal, the processor 142 may instruct the vehicle user to pull over and may actuate the vehicle user inebriation test.

In yet another aspect, the processor 142 may actuate the vehicle user inebriation test when the processor 142 determines that the vehicle user may be fatigued. In some aspects, the processor 142 may determine that the vehicle user may be fatigued by measuring vehicle user eye closure percentage, when the vehicle user is driving the vehicle 102 or otherwise. For example, a vehicle camera (e.g., a vehicle driver tracking camera or a vehicle occupant camera) may capture vehicle user eyes and may send the captured eye information to the processor 142. Responsive to receiving the eye information, the processor 142 may determine (e.g., by using deep or convolutional neural network architecture and/or training set) whether the vehicle user eye closure percentage is greater than a predetermined threshold. Responsive to determining that the closure percentage is greater than the predetermined threshold, the processor 142 may determine that the vehicle user may be fatigued and may actuate the inebriation test (or may actuate the general vehicle user focus test before actuating the inebriation test).

In further aspects, the processor 142 may determine whether the vehicle user may be fatigued by evaluating a Vestibulo-Ocular Reflex (VOR) of the vehicle user which may be caused in response to vehicle movement (e.g., when the vehicle user drives the vehicle 102). Specifically, the processor 142 may evaluate vehicle user's VOR performance to determine whether the vehicle user may be fatigued.

In other aspects, the processor 142 may determine whether the vehicle user may be fatigued by measuring additional vehicle user parameters. For example, the processor 142 may determine a vehicle user engagement level with the vehicle steering wheel (not shown in FIG. 1), to determine whether the vehicle user is fatigued. In particular, the processor 142 may determine, via a vehicle user steering wheel sensor (not shown in FIG. 1) if the vehicle user is holding or engaging with the steering wheel too loosely or too tightly. Based on the determination of an abnormal engagement level, the processor 142 may determine that the vehicle user may be fatigued and may actuate the inebriation test (or may actuate the general vehicle user focus test before actuating the inebriation test).

In some aspects, the vehicle user may request the processor 142 to actuate the inebriation test. For example, the vehicle user may send a request, via a vehicle user device or the infotainment system 152, to the processor 142 to actuate the inebriation test, if the vehicle user wants to check whether he is fit to drive the vehicle 102. Responsive to receiving the request from the vehicle user, the processor 142 may actuate the inebriation test.

Responsive to the inebriation test actuation, the first detector 154 may detect a vehicle user's body portion inside the vehicle 102. In particular, the first detector 154 may be configured to detect a vehicle user's head posture. In one or more aspects, the first detector 154 may include a vehicle interior camera(s), a vehicle driver tracking camera, a vehicle occupant camera, and/or any other vehicle component configurable to detect the vehicle user's head posture. In some aspects, the first detector 154 may monitor/track the vehicle user's head posture regularly and/or at predetermined intervals, when the processor 142 actuates the inebriation test.

In some aspects, the processor 142 may be configured to receive the vehicle user head posture information from the first detector 154. Responsive to receiving the head posture information, the processor 142 may store the information in the memory 144. In particular, the processor 142 may store the head posture information in a vehicle user head posture (UHP) database 146. In addition, the processor 142 may determine whether the head posture is in a predefined alignment, based on the received information. In some aspects, the predefined alignment may include the head posture being straight (and not oriented sideways, upwards or downwards).

In a scenario where the processor 142 determines that the head posture is in the predefined alignment, the processor 142 may initiate a vehicle user eye movement test (e.g., a horizontal eye gaze nystagmus test), described below. On the other hand, if the processor 142 determines that the head posture is not in the predefined alignment (e.g., tilted right or left), the processor 142 may provide feedback to the vehicle user to correct the head posture. For instance, the processor 142 may instruct the vehicle user, via the infotainment system 152, to look straight, upwards (or downwards), and/or the like. In some aspects, the processor 142 may instruct the user to correct the head posture alignment before starting the horizontal eye gaze nystagmus test and/or during the test. For example, the processor 142 may instruct the vehicle user to keep the head posture fixed in a straight alignment, during the horizontal eye gaze nystagmus test duration. In some aspects, the processor 142 may provide multiple feedbacks/instructions to the vehicle user, until the head posture is in the predefined alignment. The details of head posture correction may be understood in conjunction with FIG. 2.

A person ordinarily skilled in the art may appreciate that the processor 142 corrects the vehicle user head posture to perform the horizontal eye gaze nystagmus test accurately. Specifically, the horizontal eye gaze nystagmus test may involve determination of vehicle user's eye twitching or irregular eye movement, as the vehicle user rotates eyeballs in a horizontal direction (e.g., left or right) during the test. If the vehicle user's head posture is not aligned correctly, the processor 142 may not be able to determine the eye twitching and/or irregular eye movement. Therefore, the processor 142 may prompt the vehicle user to correct the vehicle user's head posture by providing instructions. In some aspects, the processor 142 may display the vehicle user's head posture on the infotainment system 152 and may further display the target posture (i.e., the predefined alignment) on the infotainment system 152, e.g., as a mannequin head. The processor 142 may wait until the vehicle user's head posture is correct. Therefore, before initiating the horizontal eye gaze nystagmus test, the processor 142 may prompt the user to correct the vehicle user's head posture, till the user corrects the head posture. In other aspects, the vehicle 102 may include a robotic arm that may physically correct the user's head posture.

Responsive to a determination that the vehicle user's head posture is in the predefined alignment, the processor 142 may initiate the horizontal eye gaze nystagmus test. In some aspects, to initiate the horizontal eye gaze nystagmus test, the processor 142 may activate a plurality of vehicle visual indicators to illuminate in a predetermined manner, and may instruct the vehicle user, via the infotainment system 152, to track the activated indicators. In particular, the processor 142 may activate the plurality of vehicle visual indicators in a sequential manner such that the vehicle user rotates the eyes in a horizontal direction, to track the activated indicators. In some aspects, the plurality of vehicle visual indicators may include Human-Machine Interface (HMI) visual components (or vehicle key-point illuminators). For instance, the visual indicators may be ambient vehicle lights, mirror blind spot indicators, overhead lamps, and/or the like. Alternatively, or additionally, the processor 142 may activate a vehicle display(s), for example a vehicle panoramic display, and may instruct the vehicle user to track the activated display. The details of vehicle visual indicator activation may be understood in conjunction with FIG. 3. In addition, the processor 142 may provide the instructions to the vehicle user 202 to track the activated indicators in the form of audio feedback (e.g., spoken text commands, via a vehicle audio system or the infotainment system 152).

In some aspects, the processor 142 may command the second detector 156 to detect or capture the vehicle user's eye movement, as the vehicle user tracks the activated indicators. The second detector 156 may include, for example, an eye gazing device or any other vehicle component (e.g., the vehicle driver tracking camera or the vehicle occupant camera) configurable to detect the vehicle user's eye movement. In some aspects, the second detector 156 may be same as the first detector 154. In other aspects, the second detector 156 may be different from the first detector 154.

In some aspects, the processor 142 may receive the vehicle user's eye movement information from the second detector 156 and may store the received information in a vehicle user eye movement (UEM) database 148. In addition, the processor 142 may determine user's eye twitching at extreme eye gazes, irregular eye movement or tracking, and/or evaluate pupil or glint trajectory throughout the testing process, based on the received eye movement information. In some aspects, the processor 142 may determine the user's eye movement by localizing the eyes using regression or other classification approaches.

Specifically, responsive to receiving the eye movement information, the processor 142 may run a single deep-learning algorithm that does multi-frame analysis, a pair of deep-learning algorithms to detect eye twitching and irregular eye movement/tracking, or a series of deterministic algorithms that evaluate pupil trajectory throughout the testing process. In some aspects, the algorithms may be deep or convolutional neural network architecture-based algorithms. For instance, the algorithms may include long short-term memory (LSTM) neural network based algorithms, recurrent neural network (RNN) based algorithms, spatiotemporo neural network based algorithms and/or the like.

In particular, the processor 142 may be configured to determine, by using deep or convolutional neural network-based algorithms, whether the vehicle user's eye movement meets a predetermined condition, based on the received eye movement information. In some aspects, the predetermined condition may be associated with a vehicle user's inebriated state. In particular, the predetermined condition may include eye twitching at extreme eye gazes or an irregular eye movement, when the vehicle user's eyes track the activated indicators. A person ordinarily skilled in the art may appreciate that the vehicle user's eyes may twitch at extreme gazes when the vehicle user is in an inebriated state.

In accordance with some aspects, the processor 142 may be configured to actuate a control action(s), responsive to the determination that the vehicle user's eye movement meets the predetermined condition. The control actions may include, for example, calling a vehicle user's friend or family, calling police, a vehicle sharing service, and/or the like. The control action details may be understood in conjunction with FIG. 4.

The processor 142 may fetch one or more instruction sets having instructions for control actions, and retrieve user profile information (user profile information not shown in FIG. 1) from the memory 144. Specifically, the memory 144 may store a vehicle user profile information in a user information (UI) database 150. The information may include, for example, vehicle username, address, contact list, information associated with user's daily activities, user's intoxicated operation history, and/or the like. In some aspects, the processor 142 may access the vehicle user's contact list to contact a friend, when the processor 142 determines that the vehicle user is in the inebriated state.

Figure 2:
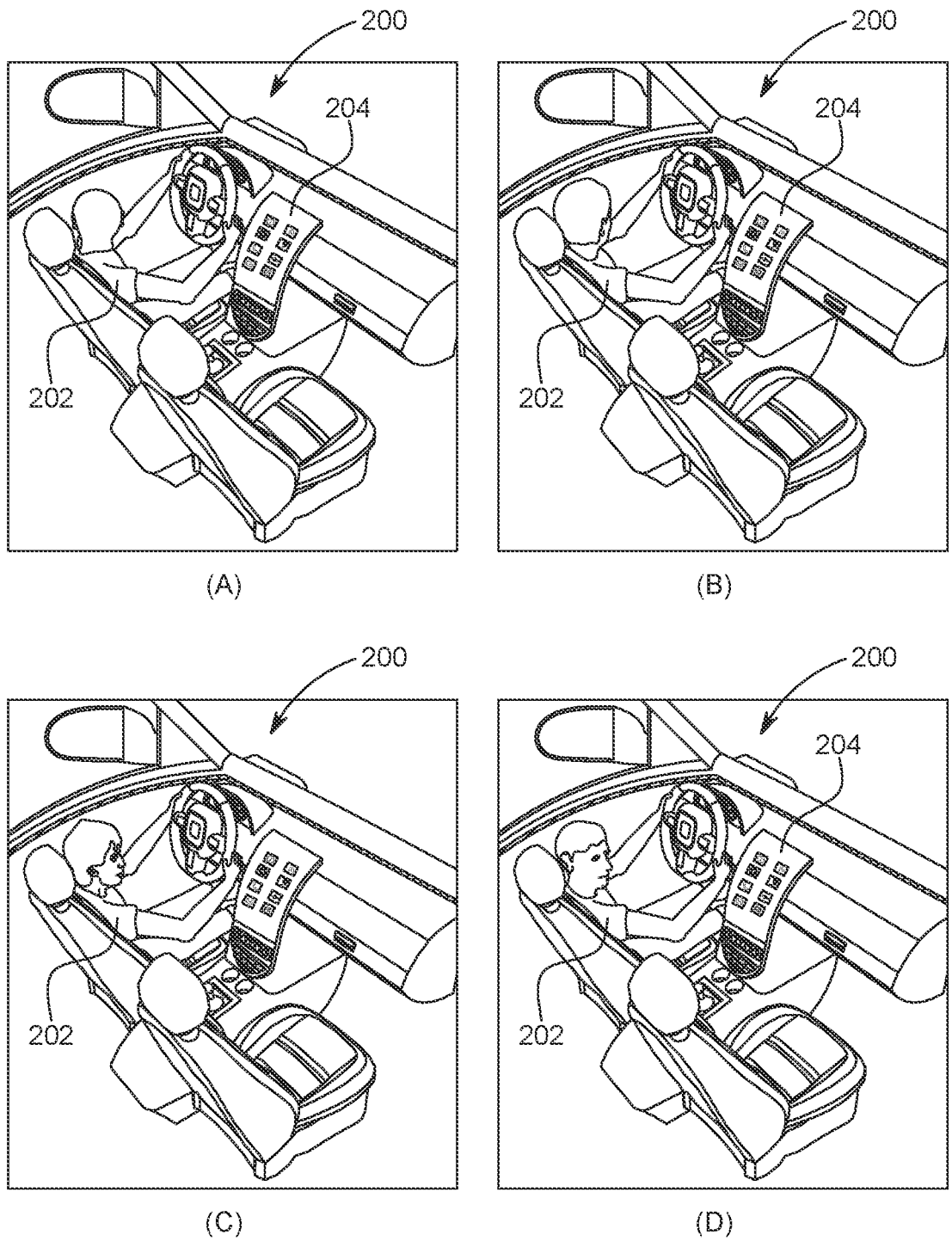
FIG. 2 depicts an example vehicle in which techniques and structures for providing the systems and methods disclosed herein may be implemented.

FIG. 2 depicts an example vehicle 200 in which techniques and structures for providing the systems and methods disclosed herein may be implemented. The vehicle 200 may be the same as the vehicle 102. A vehicle user 202 (or a driver 202) may operate the vehicle 200. As discussed above, the first detector 154 may be configured to monitor a vehicle user's head posture, when the vehicle user 202 is sitting inside the vehicle 200. In some aspects, the first detector 154 may monitor the vehicle user head posture when the processor 142 initiates the inebriation test. In some aspects, the first detector 154 may monitor the vehicle user head posture throughout the inebriation test process.

As described above, the first detector 154 may send the vehicle user head posture information to the processor 142, which may determine whether the head posture is in the predefined alignment. Responsive to a determination that the head posture is not in the predefined alignment, the processor 142 may instruct the vehicle user to correct the head posture.

For instance, if the processor 142 determines that the vehicle user head is rotated left, as shown in FIG. 2A, the processor 142 may instruct the vehicle user 202 to correct the head posture and "look straight" (e.g., in the predefined alignment). In some aspects, the processor 142 may provide the instructions to the vehicle user 202 to correct the head posture in the form of audio or video feedback (e.g., alarms or spoken text commands, via a vehicle audio system or an infotainment system 204). For example, the processor 142 may instruct the vehicle user to "rotate head to the right" or "align head with the center console" or "tilt head more towards the steering wheel", to correct the vehicle user head posture. In addition, the feedback can take the form of directional LED lights or information on the infotainment system 204 including text, arrow indicators, or a figure of a head that moves with the user's head that is displayed on the infotainment system 204.

Similarly, if the vehicle user head is rotated slightly rightwards (as shown in FIG. 2C) or towards an extreme right position (as shown in FIG. 2D), the processor 142 may instruct the vehicle user 202 to correct the head posture and may provide audio/video feedback according to the user head tilt or rotation.

In some aspects, the processor 142 may initiate the horizontal eye gaze nystagmus test, when the vehicle user 202 corrects the head posture to align straight, as shown in FIG. 2B. The process of conducting the horizontal eye gaze nystagmus test, via the processor 142, may be understood in conjunction with FIG. 3.

In some aspects, the first detector 154 may keep on monitoring the vehicle user head, even when the processor 142 initiates the horizontal eye gaze nystagmus test. In other words, even during the horizontal eye gaze nystagmus test, if the vehicle user 202 changes head position from "A" to "B", "C" or "D", the processor 142 may provide real-time instructions or feedback to the vehicle user 202 to keep the head posture fixed at position "A". This is because if the vehicle user 202 moves the head (instead of eyes) to track the visual indicators, then the processor 142 may not be able to detect the eye twitching correctly, as the vehicle user 202 may not be rotating his eyes in the required manner (and may instead be rotating his head). Hence, the inebriation test results may not be accurate if the vehicle user 202 moves the head.

In some aspects, the processor 142 may inform the vehicle user 202, via the infotainment system 204, that the vehicle user 202 does not pass the inebriation test, if the vehicle user 202 does not correct the head posture after a set number of feedback or instructions. In this case, the processor 142 may re-initiate the horizontal eye gaze nystagmus test or may determine that the vehicle user 202 is in an inebriation state (and take control actions, as described in FIG. 4). In some aspects, the processor 142 may re-initiate the horizontal eye gaze nystagmus test if the vehicle user 202 does not correct the head posture after receiving a first predefined number of feedback/instructions. Similarly, the processor 142 may determine that the vehicle user 202 is in the inebriation state if the vehicle user 202 does not correct the head posture after receiving a second predefined number of feedback/instructions. In some aspects, the second predefined number of feedback/instructions may be greater than the first predefined number of feedback/instructions.

Figure 3:
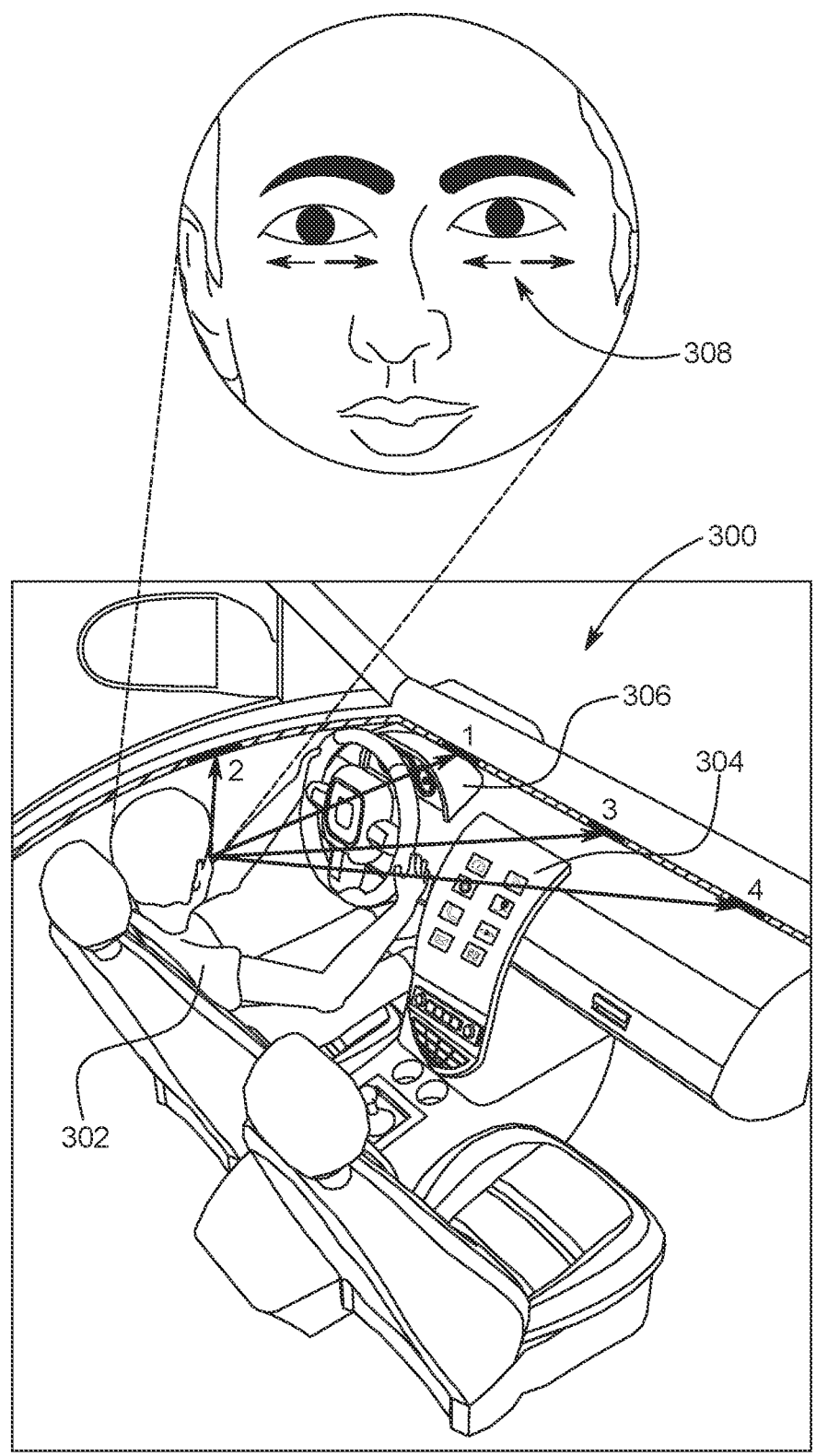
FIG. 3 illustrates an example embodiment of providing training to a vehicle user to take an inebriation test in a vehicle in accordance with the present disclosure.

FIG. 3 illustrates an example embodiment of providing training to a vehicle user 302 to take an inebriation test in a vehicle 300 in accordance with the present disclosure. The vehicle 300 may be same as the vehicle 102. In some aspects, the vehicle 300 may be configured to guide or coach the vehicle user 302 to take the inebriation test (such as the horizontal eye gaze nystagmus test) inside the vehicle 300.

In particular, the vehicle 300 may be configured to conduct the inebriation test by using a plurality of vehicle visual indicators. The vehicle visual indicators may include Human-Machine Interface (HMI) visual components (or vehicle key-point illuminators). For instance, the visual indicators may be ambient vehicle lights, mirror blind spot indicators, overhead lamps, and/or the like. Alternatively, or additionally, the vehicle 300 may be configured to conduct the test by using vehicle displays, such as one or more vehicle panoramic displays (not shown in FIG. 3), a heads-up display (HUD) (not shown in FIG. 3), or another user interface.

As discussed above, the processor 142 may activate the inebriation test when the vehicle user 302 enters the vehicle 300 and has an intoxicated operation history (based on, for example, the user profile history) when the processor 142 determines one or more predefined trigger events (e.g., when the vehicle user 302 is swerving the vehicle 300 or when the vehicle user 302 is fatigued), or when the vehicle user 302 requests inebriation test actuation.

Responsive to the inebriation test activation, the processor 142 may confirm the vehicle user head posture, as described in FIGS. 1 and 2. When the head posture is in the predetermined alignment, the processor 142 may activate the vehicle visual indicators (or vehicle display) in a predetermined manner (e.g., from one side to another to capture irregular eye twitching at extreme eye poses). The processor 142 may further instruct the vehicle user 302 to track the vehicle visual indicators without moving the head. In some aspects, the processor 142 may provide the instructions to the vehicle user 302 in the form of audio or video feedback (such as via a vehicle audio system or an infotainment system 304). In some aspects, the processor 142 may provide the instructions to the vehicle user 302 via a vehicle user device (not shown in FIG. 3) that may operatively connect with the vehicle 300.

In some aspects, as shown in FIG. 3, the processor 142 may instruct the vehicle user 302 to look straight (e.g., at the center of a vehicle steering wheel) at step 1 (shown as position "1" in FIG. 3), when the processor 142 initiates the inebriation test.

At step 2, the processor 142 may activate (e.g., turn on) a first ambient vehicle light portion towards the vehicle user's left side (shown as position "2" in FIG. 3). The processor 142 may further instruct the vehicle user 302 to track/look at the first ambient light portion "2", without moving the head.

At step 3, the processor 142 may deactivate (turn off) the first ambient light portion and may activate a second ambient light portion that is towards the vehicle user right side (shown as location "3" in FIG. 3). The processor 142 may again instruct the vehicle user 302 to track the second ambient light portion "3", without moving the head.

At step 4, the processor 142 may deactivate the second ambient light portion and may activate a third ambient light portion that is towards an extreme right side (shown as location "4" in FIG. 3). The processor 142 may repeat this process multiple times to accurately determine the inebriation test results.

In other aspects, the processor 142 may illuminate/activate different visual HMI components or the vehicle panoramic display (not shown in FIG. 3) one by one, from one side to another (in a horizontal direction), in a manner similar to the one mentioned above.

In some aspects, the vehicle 300 may include an eye detector 306 (same as the second detector 156, described in conjunction with FIG. 1). The eye detector 306 may be configured to monitor or capture a vehicle user eye movement 308 during the inebriation test (e.g., by tracking the vehicle user eye movement 308 from one side to another; specifically, by tracking pupil or glint trajectory). In some aspects, the processor 142 may be configured to communicate with the eye detector 306 and may receive the eye movement information from the eye detector 306. Responsive to receiving the eye movement information, the processor 142 may compare the eye movement 308 (captured at different angles) with respective normal eye movements (information of which may be stored in the memory 118 or the memory 144). Stated another way, the processor 142 may determine that the vehicle user eye movement 308 meets a predetermined condition. In some aspects, the predetermined condition may include twitching at extreme eye gaze or an irregular eye movement/tracking when the vehicle user's eyes track the activated vehicle visual indicators.

As described above, the processor 142 may execute a single deep-learning algorithm having multi-frame analysis, deep-learning algorithms configured and/or programmed to detect eye twitching and irregular tracking, or a series of deterministic algorithms that evaluate pupil trajectory throughout the testing process. In some aspects, the algorithms may be deep or convolutional neural network architecture-based algorithms. For instance, the algorithms may include long short-term memory (LSTM) neural network based algorithms, recurrent neural network (RNN) based algorithms, spatio-temporo neural network based algorithms and/or the like.

Responsive to determining twitching at extreme eye gazes or irregular eye movement, the processor 142 may determine that the vehicle user 302 may be in an inebriated state. The processor 142 may be further configured to actuate a control action(s), when the processor 142 determines that the vehicle user 302 is in the inebriated state. The control action details may be understood in conjunction with FIG. 4.

In accordance with further aspects, as described above in conjunction with FIG. 1, the processor 142 may be configured to conduct the general vehicle user focus test, instead of or before the inebriation test described above. For instance, the processor 142 may conduct the general vehicle user focus test when the vehicle user 302 enters the vehicle 300 and the vehicle user 302 does not have an intoxicated operation history, when the vehicle user 302 is swerving while driving the vehicle 300 or when the vehicle user is displaying fatigue indicators.

As an example, in some aspects, the processor 142 may activate the vehicle visual components (in a sequential manner) or a vehicle display system (e.g., the vehicle panoramic display), when the processor 142 conducts the general vehicle user focus test on determination of vehicle user fatigue. Responsive to visual component activation, the processor 142 may instruct the vehicle user 302 to track the activated vehicle visual components or the vehicle display system. In the general vehicle user focus test, the processor 142 may not instruct the vehicle user 302 to keep the head stationary, however the eye detector 306 may still capture the vehicle user eye movement 308. In addition, a vehicle camera (e.g., the vehicle driver tracking camera or the vehicle occupant camera) may capture the vehicle user head rotation, as the vehicle user eyes track the activated vehicle visual components. In one aspect, the processor 142 may correlate the vehicle user head movement with the vehicle user eye movement 308, to determine if the vehicle user 302 needs to take the inebriation test.

In some aspects, the processor 142 may be configured to transmit a notification or instruct, via the infotainment system 304, the vehicle user 302 to pull over and take some rest when the vehicle user 302 tracks the activated vehicle visual components (or the vehicle display system) properly. In other words, the processor 142 may determine that the vehicle user 302 may not be inebriated but may need some rest, when the vehicle user 302 tracks the activated vehicle visual components properly in the general vehicle user focus test. In some aspects, the processor 142 may determine that the vehicle user 302 may need rest (and may not be inebriated) when the correlation between the vehicle user head movement with the vehicle user eye movement 308 is greater than a predefined threshold. Alternatively, in cases where the vehicle user 302 is unable to track the activated vehicle visual components or the correlation is lower than a threshold, the processor 142 may initiate the full inebriation test (as described above) to ascertain whether the vehicle user 302 is in the inebriated state.

As another general vehicle user focus test example, the processor 142 may instruct the vehicle user 302 to manually switch on and/or off specific vehicle visual components (e.g., vehicle lights) in a predetermined manner, when the vehicle user 302 enters the vehicle 300. In this case, the processor 142 may track whether the vehicle user 302 follows the instructions properly (e.g., switches on and/or off vehicle visual components as per instructions). Responsive to a determination that the vehicle user 302 follows the instruction properly, the processor 142 may not initiate the inebriation test. Alternatively, the processor 142 may initiate the inebriation test, when the processor 142 determines that the vehicle user 302 is not following the instructions.

Figure 4:
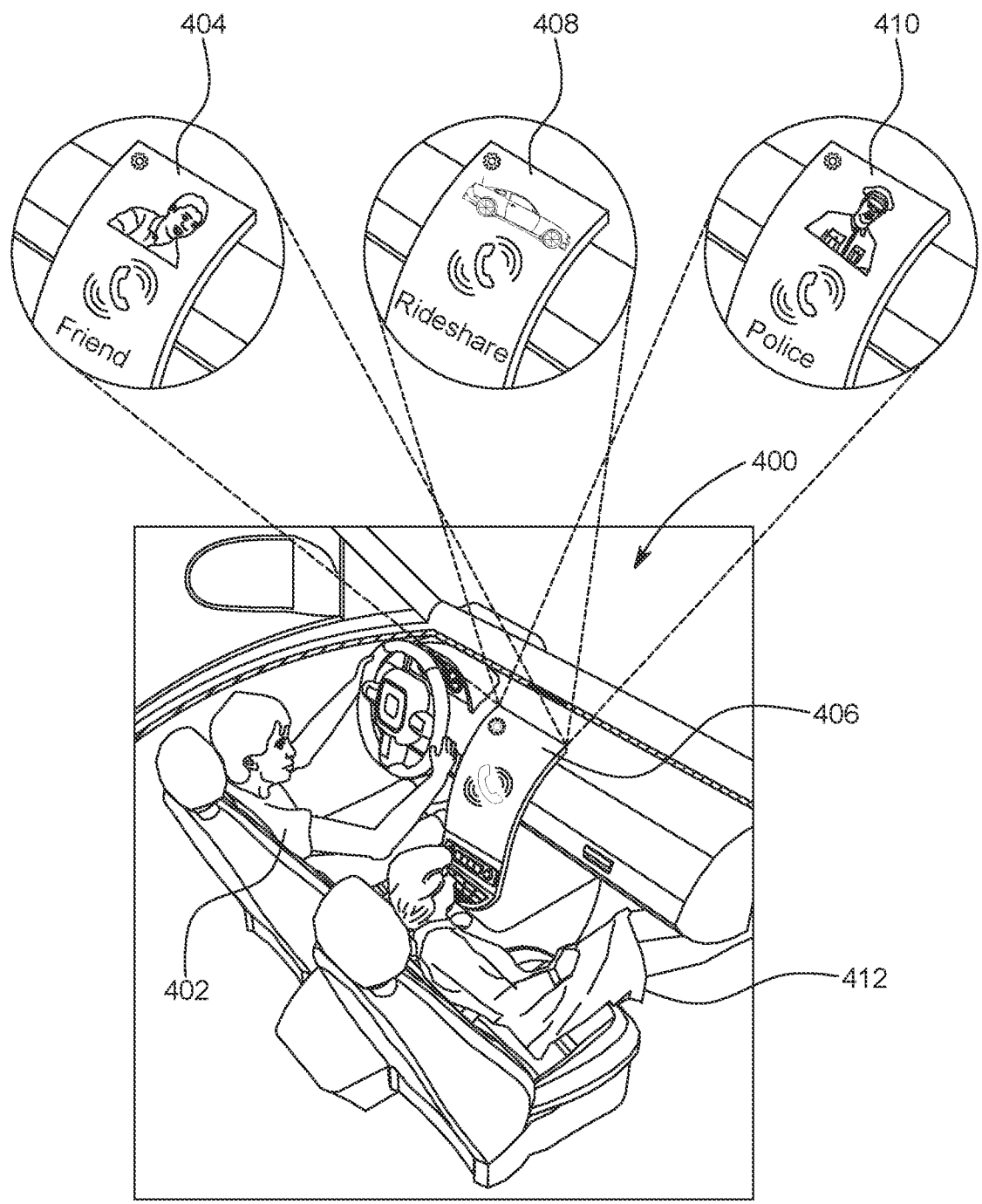
FIG. 4 illustrates an example control action(s) for mitigating intoxicated operation in accordance with the present disclosure.

FIG. 4 illustrates an example control action(s) to prevent intoxicated operation in accordance with the present disclosure. In particular, FIG. 4 depicts a vehicle 400, which may be operated by a vehicle user 402. The vehicle 400 may be same as the vehicle 102. As described above, the processor 142 may conduct an inebriation test to determine whether the vehicle user 402 is inebriated. Responsive to a determination that the vehicle user 402 is inebriated, the processor 142 may actuate an appropriate control action to prevent intoxicated operation.

For instance, when the processor 142 determines that the vehicle user 402 is inebriated, the processor 142 may fetch a vehicle user contact list from the user information database 150 stored in the memory 144. The processor 142 may be further configured to call a contact person (a mobile phone of a friend or family member) or transmit a notification to the contact person and instruct the contact person to take over the vehicle 400 as the vehicle user 402 may be inebriated (as indicated in block 404 of FIG. 4). In some aspects, the processor 142 may call the contact person via a vehicle infotainment system 406 that may be connected to a vehicle user device (not shown).

In some aspects, the processor 142 may call a vehicle rideshare network/service (as indicated in block 408 of FIG. 4) or transmit a rental vehicle request/notification to a vehicle rideshare server (not shown in FIG. 4), when the vehicle user 402 is inebriated. In this case, responsive to the rental vehicle request, the vehicle rideshare service may send the rental vehicle to the vehicle 400 location, to pick up the vehicle user 402. In one aspect, along with the rental vehicle request, the processor 142 may send a current vehicle user location and a destination vehicle user location to the vehicle rideshare server. The processor 142 may determine the current vehicle user location by using the NAV 136. Further, the processor 142 may determine the destination vehicle user location based on the vehicle user daily activity information, stored in the user information database 150. For example, the processor 142 may determine that the vehicle user 402 goes to home in the evening from the daily activity information. In this case, the processor 142 may determine the destination location to be vehicle user home (if the processor 142 determines the vehicle user 402 to be inebriated during evening time).

In further aspects, the processor 142 may be configured to call authorities (such as police, as indicated in block 410 of FIG. 4) in certain circumstances. For instance, when the vehicle user 402 is unable to clear the inebriation test a set number of times (such as 5 times) in a specific period of time (such as 1 hour), and attempts to drive the vehicle 400, the processor 142 may call the authorities. The processor 142 may also call the authorities, when the vehicle user 402 has an intoxicated operation history and attempts to drive the vehicle 400. The processor 142 may further share the vehicle location to the authorities, so that the authorities may track the vehicle movement. In other aspects, a vehicle camera (not shown in FIG. 4) may capture the vehicle user's image in an inebriated state, for record purposes.

In another scenario, the processor 142 may determine, via the sensory system 134, that the vehicle user 402 is accompanied by a passenger 412 in the vehicle 400. Responsive to the determination, the processor 142 may provide feedback/instruction, via the infotainment system 406, to the vehicle user 402 and the passenger 412 to change the driver. In other words, the processor 142 may ask the passenger 412 to drive the vehicle 400. In such scenarios, the processor 142 may trigger an inebriation test for the passenger 412, to determine whether the passenger 412 is fit for driving. In this case, the processor 142 may allow the passenger 412 to drive the vehicle 400, when the processor 142 determines that the passenger 412 is not inebriated. The processor 142 may conduct the inebriation test for the passenger 412 in the same manner as that for the vehicle user 402.

In some aspects, the processor 142 may be configured to prevent vehicle start, when the vehicle user 402 is unable to clear the inebriation test, to prevent intoxicated operation. In other aspects, the processor 142 may transmit a notification (audio or video), via the infotainment system 152, to the vehicle user 402 informing about the intoxicated operation effects, to dissuade the vehicle user 402 from driving the vehicle 400.

In addition, when the processor 142 determines that the vehicle user 402 is fatigued (as discussed in conjunction with FIGS. 1 and 3), the processor 142 may control the vehicle operation. For instance, the processor 142 may control vehicle speed, when the processor 142 determines that the vehicle user 402 may be fatigued, and another vehicle is close to the vehicle 400.

Figure 5:
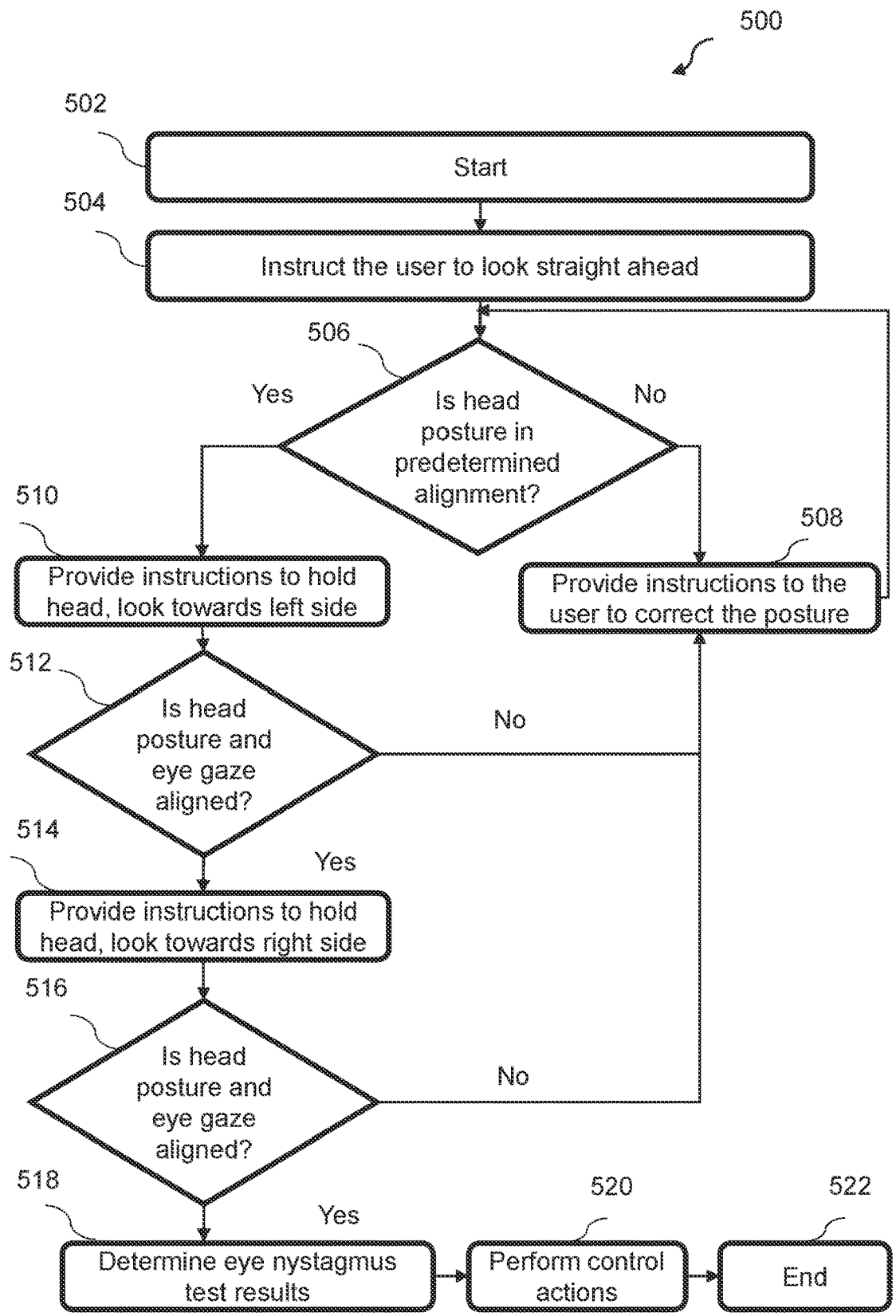
FIG. 5 depicts a first flow diagram of an example method for providing training to a vehicle user to take an inebriation test, in accordance with the present disclosure.

FIG. 5 depicts a first flow diagram of an example method 500 for providing training to a vehicle user to take an inebriation test, in accordance with the present disclosure. In particular, the method 500 describes a process to provide training to the vehicle user through vehicle audio systems, for example audio HMI components (without activating/illuminating the vehicle visual indicators). The following process is exemplary and not confined to the steps described hereafter. Moreover, alternative embodiments may include more or less steps that are shown or described herein and may include these steps in a different order than the order described in the following example embodiments.

The method 500 starts at step 502. At step 504, the method 500 may include instructing, via the processor 142, the vehicle user to look straight ahead. At step 506, the method 500 may include determining, via the processor 142, whether the vehicle user head posture is in a predetermined alignment (as discussed above). When the processor 142 determines that the head posture is not in the predetermined alignment, the method 500 moves to step 508. At step 508, the method 500 may include providing instructions, via the processor 142, to the vehicle user to correct the head posture. For example, the processor 142 may transmit, via the infotainment system 152, audio commands to tilt the head towards the center console, tilt left, and/or the like, when the vehicle user head posture is not in the predetermined alignment. Responsive to the audio command transmission at the step 508, the method 500 may move back to the step 506. In other words, the processor 142 may check whether the vehicle user head posture is in the predetermined alignment, when the processor 142 transmits the audio commands.

In some aspects, when the processor 142 determines that the vehicle user head posture is in the predetermined alignment, the method 500 moves to step 510. At step 510, the method 500 may include providing instructions, via the processor 142, to the vehicle user to hold the head and look towards a left side (such as towards a left vehicle mirror). In some aspects, the processor 142 may provide an audio instruction to the vehicle user, for example "Keep your head straight, and move your eyes to the left".

At the step 512, the method 500 may include determining, via the processor 142, whether the vehicle user head posture and the eye gaze are aligned, according to the instructions provided at the step 510. If they are not aligned, then the method 500 moves back to the step 508. If the vehicle user head posture and the eye gaze are aligned, then the processor 142 may provide an indication that they are aligned (such as by playing a chime or a confirmation audio sound), and the method 500 may move to step 514.

At step 514, the method 500 may include providing, via the processor 142, instructions to the vehicle user to hold the head and look towards a right side (such as towards a right vehicle mirror). At step 516, the processor 142 may determine whether the vehicle user head posture and the eye gaze are aligned, according to the instructions provided at the step 514. If they are not aligned, then the method 500 may move back to the step 508. If the vehicle user head posture and the eye gaze are aligned, then the processor 142 may provide the indication that they are aligned (such as by playing the chime or the confirmation audio sound), and the method 500 may move to step 518. At step 518, the method 500 may include determining, via the processor 142, a horizontal eye nystagmus test results (as discussed above), based on the vehicle user eye movement. At step 520, the method 500 may include performing, via the processor 142, control action(s) based on the test results (as described in conjunction with FIG. 4). The method 500 ends at step 522.

Figure 6:
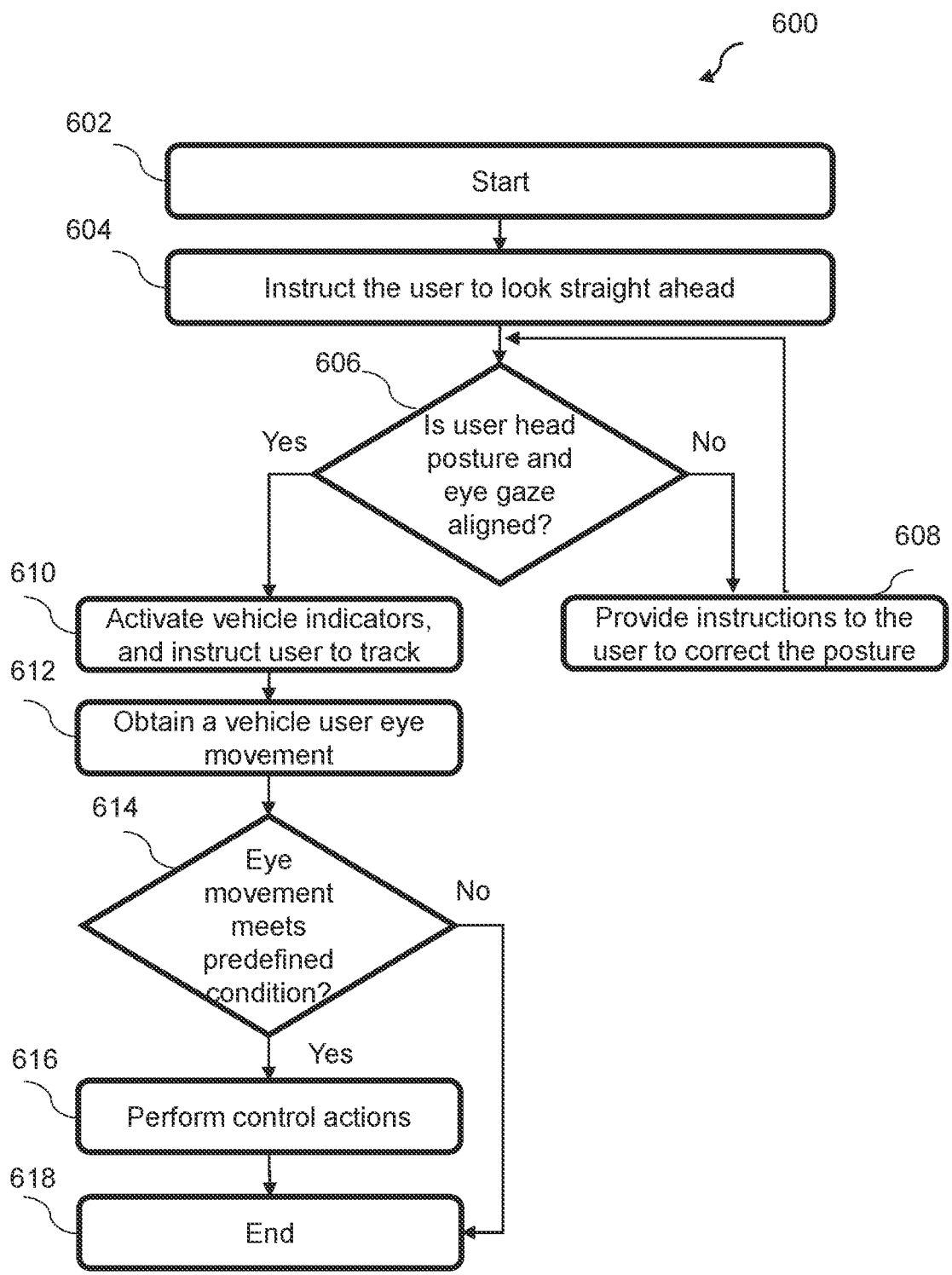
FIG. 6 depicts a second flow diagram of an example method for providing training to a vehicle user to take an inebriation test, in accordance with the present disclosure.

FIG. 6 depicts a second flow diagram of an example method 600 for providing training to a vehicle user to take an inebriation test, in accordance with the present disclosure. The method 600 starts at step 602. At step 604, the method 600 may include instructing, via the processor 142, the vehicle user to look straight ahead. At step 606, the method 600 may include determining, via the processor 142, whether the vehicle user head posture is in a predetermined alignment (as discussed above). When the processor 142 determines that the head posture is not in the predetermined alignment, the method 600 moves to step 608. At step 608, the method 600 may include providing instructions, via the processor 142, to the vehicle user to correct the head posture. Responsive to providing the instructions, the method 600 may move back to the step 606.

In some aspects, when the processor 142 determines that the vehicle user head posture is in the predetermined alignment, the method 600 moves to step 610. At step 610, the method 600 may include activating, via the processor 142, vehicle visual indicators to illuminate in a predetermined manner (from one side to another, in a sequential manner, as described above in conjunction with FIG. 3), and instructing the vehicle user to track the illuminated visual indicators. At step 612, the method 600 may include detecting, via the processor 142, vehicle user eye movement (that may be captured via the eye detector 306, as discussed above). At step 614, the method 600 may include determining, via the processor 142, whether the eye movement meets a predetermined condition. In particular, the predetermined condition may include twitching at extreme eye gazes or an irregular eye movement/tracking, when the vehicle user eyes track the activated indicators.

In some aspects, when the processor 142 determines that the eye movement meets the predetermined condition (e.g., when the processor 142 determines that the vehicle user may be intoxicated) at the step 614, the method 600 moves to step 616. At step 616, the method 600 may include performing, via the processor 142, control actions to prevent intoxicated operation, as discussed in conjunction with FIG. 4. Alternatively, when the processor 142 determines that the eye movement does not meet the predetermined condition at the step 614, the method 600 moves to step 618, at which the method 600 stops.

In some aspects, the step 606 may be performed throughout the method 500. In other words, as described above, the processor 142 may track the vehicle user head posture alignment, even when the vehicle user moves the eyes. The processor 142 may provide instructions to the vehicle user to correct head posture, as and when the vehicle user tilts the head during the method 500.

In the above disclosure, reference has been made to the accompanying drawings, which form a part hereof, which illustrate specific implementations in which the present disclosure may be practiced. It is understood that other implementations may be utilized, and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a feature, structure, or characteristic is described in connection with an embodiment, one skilled in the art will recognize such feature, structure, or characteristic in connection with other embodiments whether or not explicitly described.

Further, where appropriate, the functions described herein can be performed in one or more of hardware, software, firmware, digital components, or analog components. For example, one or more application specific integrated circuits (ASICs) can be programmed to carry out one or more of the systems and procedures described herein. Certain terms are used throughout the description and claims to refer to particular system components. As one skilled in the art will appreciate, components may be referred to by different names. This document does not intend to distinguish between components that differ in name, but not function.

It should also be understood that the word "example" as used herein is intended to be non-exclusionary and non-limiting in nature. More particularly, the word "example" as used herein indicates one among several examples, and it should be understood that no undue emphasis or preference is being directed to the particular example being described.

A computer-readable medium (also referred to as a processor-readable medium) includes any non-transitory (e.g., tangible) medium that participates in providing data (e.g., instructions) that may be read by a computer (e.g., by a processor of a computer). Such a medium may take many forms, including, but not limited to, non-volatile media and volatile media. Computing devices may include computer-executable instructions, where the instructions may be executable by one or more computing devices such as those listed above and stored on a computer-readable medium.

With regard to the processes, systems, methods, heuristics, etc. described herein, it should be understood that, although the steps of such processes, etc. have been described as occurring according to a certain ordered sequence, such processes could be practiced with the described steps performed in an order other than the order described herein. It further should be understood that certain steps could be performed simultaneously, that other steps could be added, or that certain steps described herein could be omitted. In other words, the descriptions of processes herein are provided for the purpose of illustrating various embodiments and should in no way be construed so as to limit the claims.

Accordingly, it is to be understood that the above description is intended to be illustrative and not restrictive. Many embodiments and applications other than the examples provided would be apparent upon reading the above description. The scope should be determined, not with reference to the above description, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

All terms used in the claims are intended to be given their ordinary meanings as understood by those knowledgeable in the technologies described herein unless an explicit indication to the contrary is made herein. In particular, use of the singular articles such as "a," "the," "said," etc. should be read to recite one or more of the indicated elements unless a claim recites an explicit limitation to the contrary. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A method to prevent intoxicated vehicle operation, the method comprising:
   obtaining, via a processor, vehicle user body portion posture from a first vehicle detector;
   determining, via the processor, whether the vehicle user body portion posture is in a predefined alignment;
   activating, via the processor, a plurality of vehicle visual indicators to illuminate in a predefined manner, responsive to the determination that the vehicle user body portion posture is in the predefined alignment;
   generating, via the processor, an instruction to move vehicle user eyes;
   obtaining, via the processor, a vehicle user eye movement information based on the instruction, from a second vehicle detector;
   determining, via the processor, based on the user eye movement information, that a vehicle user meets a predetermined condition, wherein the predetermined condition is associated with a vehicle user inebriated state; and
   actuating, via the processor, a control action responsive to the determination that the user eye movement meets the predetermined condition.

2. The method of claim 1 further comprising:
   providing, via the processor, output instructing the vehicle user to correct the vehicle user body portion posture, based on a determination that the vehicle user body portion posture is not in the predefined alignment; and
   obtaining, via the processor, the vehicle user body portion posture responsive to providing the output.

3. The method of claim 1, wherein the first vehicle detector is configured to detect a vehicle user head posture.

4. The method of claim 1, wherein the plurality of vehicle visual indicators comprises Human-Machine Interface (HMI) visual components or a vehicle display.

5. The method of claim 1, wherein the predetermined condition comprises twitching at extreme eye gazes or an irregular eye tracking when the vehicle user eyes track the plurality of vehicle visual indicators.

6. The method of claim 1, wherein activating the plurality of vehicle visual indicators to illuminate in the predefined manner comprises illuminating the plurality of vehicle visual indicators in a sequential manner and in a horizontal direction.

7. The method of claim 1, wherein the control action comprises at least one of: disabling a vehicle start, transmitting a vehicle user inebriated state notification to an acquaintance user device or a vehicle ridesharing server, and providing an instruction to a non-inebriated vehicle passenger to drive a vehicle.

8. A vehicle for preventing intoxicated operation, the vehicle comprising:
a first vehicle detector configured to detect a vehicle user body portion posture;
a second vehicle detector configured to detect a vehicle user eye movement; and
a processor communicatively coupled to the first vehicle detector and the second vehicle detector, wherein the processor is configured to:
provide instructions to a vehicle user to position the vehicle user body portion posture in a predefined alignment;
obtain the vehicle user body portion posture from the first vehicle detector;
determine whether the vehicle user body portion posture is in the predefined alignment;
activate a plurality of vehicle visual indicators to illuminate in a predefined manner, responsive to the determination that the vehicle user body portion posture is in the predefined alignment;
generate an instruction to move vehicle user eyes;
obtain a vehicle user eye movement information based on the instructions, from the second vehicle detector;
determine, based on the user eye movement information, that a user meets a predetermined condition, wherein the predetermined condition is associated with a vehicle user inebriated state; and
actuate a control action responsive to the determination that the vehicle user eye movement meets the predetermined condition.

9. The vehicle of claim 8, wherein the processor is further configured to:
generate a second instruction to correct the vehicle user body portion posture, based on a determination that the vehicle user body portion posture is not in the predefined alignment; and
obtain the vehicle user body portion posture responsive to providing the instruction.

10. The vehicle of claim 8, wherein the first vehicle detector is configured to detect a vehicle user head posture.

11. The vehicle of claim 8, wherein the plurality of vehicle visual indicators comprises Human-Machine Interface (HMI) visual components or a vehicle display.

12. The vehicle of claim 8, wherein the predetermined condition comprises twitching at extreme eye gazes or an irregular eye tracking when the vehicle user eyes track the plurality of vehicle visual indicators.

13. The vehicle of claim 8, wherein the processor activates the plurality of vehicle visual indicators by illuminating the plurality of vehicle visual indicators in a sequential manner and in a horizontal direction.

14. The vehicle of claim 8, wherein the control action comprises at least one of: disabling a vehicle start, transmitting a vehicle user inebriated state notification to an acquaintance user device or a vehicle ridesharing server, and providing an instruction to a non-inebriated vehicle passenger to drive a vehicle.

15. A non-transitory computer-readable storage medium having instructions stored thereupon which, when executed by a processor, cause the processor to:
provide instructions to a vehicle user to position a vehicle user body portion posture in a predefined alignment;
obtain the vehicle user body portion posture from a first vehicle detector;
determine whether the vehicle user body portion posture is in the predefined alignment;
activate a plurality of vehicle visual indicators to illuminate in a predefined manner, responsive to the determination that the vehicle user body portion posture is in the predefined alignment;
generate an instruction to move vehicle user eyes to track the plurality of vehicle visual indicators;
obtain a vehicle user eye movement information based on the instructions, from a second vehicle detector;
determine, based on the vehicle eye movement information, that a vehicle user eye movement meets a predetermined condition, wherein the predetermined condition is associated with a vehicle user inebriated state; and
actuate a control action responsive to the determination that the vehicle user eye movement meets the predetermined condition.

16. The non-transitory computer-readable storage medium of claim 15, further comprising:
providing, via the processor, output instructing the vehicle user to correct the vehicle user body portion posture, based on a determination that the vehicle user body portion posture is not in the predefined alignment; and
obtaining, via the processor, the vehicle user body portion posture responsive to providing the output.

17. The non-transitory computer-readable storage medium of claim 15, wherein the first vehicle detector is configured to detect a vehicle user head posture.

18. The non-transitory computer-readable storage medium of claim 15, wherein the plurality of vehicle visual indicators comprises Human-Machine Interface (HMI) visual components or a vehicle display.

19. The non-transitory computer-readable storage medium of claim 15, wherein the predetermined condition comprises twitching at extreme eye gazes or an irregular eye tracking when the vehicle user eyes track the plurality of vehicle visual indicators.

20. The non-transitory computer-readable storage medium of claim 15, wherein activating the plurality of vehicle visual indicators to illuminate in the predefined manner comprises illuminating the plurality of vehicle visual indicators in a sequential manner and in a horizontal direction.

* * * * *